United States Patent
Zhao et al.

(10) Patent No.: US 11,591,370 B2
(45) Date of Patent: Feb. 28, 2023

(54) PEPTOID COMPOUND AND MANUFACTURING METHOD THEREOF, OLIGOMER, PHARMACEUTICAL COMPOSITION, AND KIT

(71) Applicants: BEIJING BOE TECHNOLOGY DEVELOPMENT CO., LTD., Beijing (CN); BOE TECHNOLOGY GROUP CO., LTD., Beijing (CN)

(72) Inventors: Zijian Zhao, Beijing (CN); Yudan Yin, Beijing (CN)

(73) Assignees: BEIJING BOE TECHNOLOGY DEVELOPMENT CO., LTD., Benjing (CN); BOE TECHNOLOGY GROUP CO., LTD., Beijing (CN)

( * ) Notice: Subject to any disclaimer, the term of this patent is extended or adjusted under 35 U.S.C. 154(b) by 283 days.

(21) Appl. No.: 16/646,320

(22) PCT Filed: Aug. 22, 2019

(86) PCT No.: PCT/CN2019/102009
§ 371 (c)(1),
(2) Date: Mar. 11, 2020

(87) PCT Pub. No.: WO2020/063216
PCT Pub. Date: Apr. 2, 2020

(65) Prior Publication Data
US 2021/0206808 A1 Jul. 8, 2021

(30) Foreign Application Priority Data
Sep. 28, 2018 (CN) .......................... 201811138563.1

(51) Int. Cl.
| | |
|---|---|
| *A61K 38/00* | (2006.01) |
| *C07K 14/00* | (2006.01) |
| *C07K 1/04* | (2006.01) |
| *C07K 1/08* | (2006.01) |
| *G01N 21/64* | (2006.01) |
| *G01N 33/574* | (2006.01) |

(52) U.S. Cl.
CPC .............. *C07K 14/001* (2013.01); *C07K 1/04* (2013.01); *C07K 1/08* (2013.01); *G01N 21/6428* (2013.01); *G01N 33/57415* (2013.01); *G01N 33/57446* (2013.01); *G01N 33/57449* (2013.01); *A61K 38/00* (2013.01); *G01N 2021/6439* (2013.01); *G01N 2410/00* (2013.01)

(58) Field of Classification Search
None
See application file for complete search history.

(56) References Cited

FOREIGN PATENT DOCUMENTS

| | | |
|---|---|---|
| CN | 105753940 A | 7/2016 |
| CN | 106581700 A | 4/2017 |
| CN | 106854233 A | 6/2017 |
| CN | 106866794 A | 6/2017 |

OTHER PUBLICATIONS

Zhu et al., Antibody-Mimetic Peptoid Nanosheet for Label Free Serum-Based Diagnosis of Alzheimer's Disease AdVoMater, 2017, p. 1-7, Issue 30, vol. 29, 1700057.
Zhao J. et al., Antiamyloidogenic Activity of Aβ42-Binding Peptoid in Modulating Amyloid Oligomerization, Small, Jan. 4, 2017, Issue 1, vol. 13, , p. 1-10, Beijing China.

*Primary Examiner* — Thomas S Heard
(74) *Attorney, Agent, or Firm* — Dilworth & Barrese, LLP.; Michael J. Musella, Esq.

(57) ABSTRACT

A peptoid compound, a manufacturing method of a peptoid compound, an oligomer, a pharmaceutical composition, use of the pharmaceutical composition in the preparation of a medicament for detecting or diagnosing a disease related to tyrosine kinase HER2, and a kit for identifying circulating tumor cells are provided, the peptoid compound includes: a cysteine (Cys) subunit, a butanediamine (Nlys) subunit, a 3,4-methylenedioxybenzylamine (Npip) subunit, a 3-aminopropanic acid (Nce) subunit and a 1-naphthylamine (Na) subunit, and both the peptoid compound and the oligomer have a strong ability to bind to HER2 protein on surfaces of circulating tumor cells (CTCs), and a technology of diagnosing breast cancer on the basis of the peptoid compound can realize non-invasive and label-free rapid diagnosis, in addition, the methods for synthesizing the peptoid compound and the oligomer are simple, the preparation efficiency is high, and the production cost is low.

6 Claims, 3 Drawing Sheets

PEPTOID COMPOUND AND MANUFACTURING METHOD THEREOF, OLIGOMER, PHARMACEUTICAL COMPOSITION, AND KIT

The present application claims the priority of the Chinese Patent Application No. 201811138563.1 filed on Sep. 28, 2018, the present disclosure of which is incorporated herein by reference in its entirety as part of the present disclosure.

TECHNICAL FIELD

Embodiments of the present disclosure relate to a peptoid compound, a manufacturing method of a peptoid compound, an oligomer, a pharmaceutical composition, use of the pharmaceutical composition in the preparation of a medicament for detecting or diagnosing a disease related to tyrosine kinase HER2, and a kit for identifying circulating tumor cells.

BACKGROUND

Breast cancer and ovarian cancer are malignant tumors susceptible to women, accounting for 15% of women's cancers, and gastric cancer is also a disease with a relatively high incidence. Currently, patients with the breast cancer, the ovarian cancer and the gastric cancer are often clinically treated with anti-tumor drugs. For example, the anti-tumor drugs include cytotoxic chemotherapy drugs and protein drugs such as antibodies. However, the cytotoxic chemotherapy drugs have poor selectivity, large toxic and side effects, and are likely to cause adverse reactions; the protein drugs such as the antibodies have high specificity and small toxic and side effects, but they are likely to cause immune response and drug dependency due to their high molecular masses and complex structure, moreover, the process of preparing the protein drugs such as the antibodies is very complicated, so that the protein drugs such as the antibodies are too expensive to afford for ordinary tumor patients.

In the early stage of cancer development, circulating tumor cells (CTCs) screening technology is used to diagnose cancer. The CTCs screening test need to capture the circulating tumor cells from blood. The detection process is closely related to probe molecules coupled on the surface of the capture device, and a specific capture is achieved by the affinity of the probe molecule with the surface proteins of the CTCs. For example, the probe molecule includes a targeting molecule of a specific receptor protein at the tumor site such as antibody, polypeptide, peptoid and aptamer. Among various targeting molecules, peptoid small molecules have many advantages, such as, low immunogenicity, good tissue permeability, low molecular weight, high stability, easiness of modification, and economical efficiency and so on.

SUMMARY

At least one embodiment of the present disclosure provides a peptoid compound, and the peptoid compound comprises: a cysteine (Cys) subunit, a butanediamine (Nlys) subunit, a 3,4-methylenedioxybenzylamine (Npip) subunit, 3-aminopropanic acid (Nce) subunit, and 1-naphthylamine (Na) subunit.

For example, in the peptoid compound provided by at least one embodiment of the present disclosure, the peptoid compound comprises subunits in an order of: cysteine (Cys) subunit-butanediamine (Nlys) subunit-butanediamine (Nlys) subunit-butanediamine (Nlys) subunit-3,4-methylenedioxybenzylamine (Npip) subunit-3-aminopropanic acid (Nce) subunit-1-naphthylamine (Na) subunit.

For example, in the peptoid compound provided by at least one embodiment of the present disclosure, the peptoid compound has a structure of Formula (I):

Formula (I)

At least one embodiment of the present disclosure further provides a manufacturing method of a peptoid compound, and the manufacturing method comprises synthesizing the subunits by a solid phase synthetic method.

For example, in the manufacturing method provided by at least one embodiment of the present disclosure, the manufacturing method comprises:

(1) according to a linking order of subunits of the peptoid compound, linking a first subunit of the peptoid compound onto a solid phase support;

(2) reacting bromoacetic acid with an amino group of the first subunit linked to the solid phase support under the activation of an activator to form an amide bond;

(3) reacting a donor of a second subunit of the peptoid compound with a product obtained from step (2) to replace a bromine atom and complete the linking of the second subunit;

(4) repeating reaction with bromoacetic acid and linking of subsequent subunits, until all the subunits are linked;

(5) cleaving the synthesized peptoid compound from the solid phase support to obtain the peptoid compound.

At least one embodiment of the present disclosure further provides an oligomer, and the oligomer comprises a molecular structure formula of:

in which 10≥n1≥3, 10≥n2≥3, n1=n2, and both n1 and n2 are natural numbers.

For example, in the oligomer provided by at least one embodiment of the present disclosure, the molecular structure formula of the oligomer is:

kit comprises: a housing, a microfluidic chip disposed in the housing, and a fluorescent probe disposed in the housing, and the fluorescent probe is any one of the oligomers mentioned above with a fluorescent label.

At least one embodiment of the present disclosure further provides a pharmaceutical composition, and the pharmaceutical composition comprises: any one of the oligomers mentioned above, and a pharmaceutically acceptable adjuvant.

For example, in the pharmaceutical composition provided by at least one embodiment of the present disclosure, the adjuvant comprises at least one of an excipient, a diluent, a carrier, a flavoring agent, a binder, and a filler.

At least one embodiment of the present disclosure further provides use of any one of the pharmaceutical compositions mentioned above in the preparation of a medicament for detecting or diagnosing a disease related to tyrosine kinase HER2.

For example, in the use provided by at least one embodiment of the present disclosure, the disease comprises at least one of breast cancer, gastric cancer, and ovarian cancer.

At least one embodiment of the present disclosure further provides a kit for identifying circulating tumor cells, and the

BRIEF DESCRIPTION OF THE DRAWINGS

In order to clearly illustrate the technical solution of the embodiments of the present disclosure, the drawings of the embodiments will be briefly described. It is apparent that the described drawings are only related to some embodiments of the present disclosure and thus are not limitative of the present disclosure.

DETAILED DESCRIPTION

In order to make the objectives, technical solutions, and advantages of the embodiments of the present disclosure clearer, the technical solutions of the embodiments of the present disclosure will be clearly and completely described below with reference to the accompanying drawings of the embodiments of the present disclosure. Obviously, the described embodiments are not all, but some embodiments of the present disclosure. Based on the described embodiments of the present disclosure, any other embodiment which can be obtained by a person of ordinary skill in the art without creative labor fall within the scope of the present disclosure.

Unless otherwise defined, all the technical and scientific terms used herein have the same meanings as commonly understood by one of ordinary skill in the art to which the present disclosure belongs. The terms "first," "second," etc., which are used in the description and claims of the present disclosure, are not intended to indicate any sequence, amount or importance, but distinguish various components. The terms "comprises," "comprising," "includes," "including," etc., are intended to specify that the elements or the objects stated before these terms encompass the elements or the objects listed after these terms as well as equivalents thereof, but do not exclude other elements or objects.

Unless otherwise specified, experimental methods used in the following examples are conventional methods. Unless otherwise specified, all the materials and reagents used in the following examples can be obtained from commercial sources.

In the following examples, the model of the SPRi instrument is Plexera Kx5V2, Plexera Bioscience LLC, USA. The instrument is mainly equipped with a 660 nm LED light source, a CCD image collector and a sensor chip with a microfluidic channel. The instrument shows changes of the reflected light intensity over time at each monitoring points and records changes as an SPR curve.

Unless otherwise specified, In the article "µM" refers to "µmol/L", and "mM" refers to "mmol/L".

Due to the heterogeneity of tumors, for a patient whose cancer cells have metastasized, simply taking tumor tissue from a certain location is not sufficient to reflect the overall condition of the patient, however, it is impractical to take samples from all tumor tissues in the patient, therefore, a tissue biopsy technology is limited. A liquid biopsy technology is not required to take sample from the tumor tissue in the patient, but merely needs to take sample from the blood or secretions of the patient. Therefore, researchers pay increasingly attention and do more and more research into the liquid biopsy technology. The liquid biopsy technology comprises detecting circulating tumor cells (CTCs), circulating tumor DNA (ctDNA), or exosomes with the peptoid compound.

Circulating Tumor Cells (CTCs) are a collective name for various types of tumor cells that exist in peripheral blood, which are shed from solid tumor lesions (primary lesions, metastatic lesions) due to spontaneous or diagnostic operations. Most of CTCs undergo apoptosis or are swallowed after entering the peripheral blood, and few CTCs can escape and develop into metastatic lesions, thereby increasing the risk of death in patients with malignant tumors. The presence or absence of the CTCs and the number of the CTCs are important indicators for judging cancer progression and metastasis. Detecting and tracking the number of the CTCs in the peripheral blood helps early screening, curative effect monitoring, prognostic judgment and recurrence prediction of the patients.

The detection technology for the CTCs can predict the occurrence of early tumors, and can detect the tumor metastasis during the treatment of patients with drugs. In addition, it can also guide medication for subsequent treatment. The CTCs are originated from primary tumors or metastatic tumors, and the CTCs can enter blood vessels after detaching from the basement membrane. Because the content of the CTCs in the blood is extremely low, and a size of each of the CTCs is similar to a size of a white blood cell, which makes that it is difficult to detect CTCs by using the liquid biopsy technology. However, a surface of each of the CTCs carries proteins which have high specific expression against the related cancers. For example, human epithelial growth factor receptor (HER for short) includes EGFR/ErbB1/HER1, ErbB2/HER2, ErbB3/HER3, and ErbB4/HER4. Human epidermal growth factor receptor-2 (HER2) overexpressing breast cancer is a major type of the breast cancer, and HER2 overexpressing ovarian cancer and HER2 overexpressing gastric cancer are also common. Therefore, specifically identifying the HER2 protein on the surfaces of the CTCs in patients with the HER2 overexpressing breast cancer, with the HER2 overexpressing ovarian cancer, and with the HER2 overexpressing gastric cancer provides a favorable guarantee for capturing the corresponding CTCs with high sensitivity. For example, molecular probes with high affinity and high sensitivity for the HER2 protein can be designed.

Peptoid small molecules have characteristics of low immunogenicity, good tissue permeability, small molecular weight, high stability, easy modification and low manufacturing cost, and so on. However, in the application of molecular probes, the binding ability of the peptoid small molecules and biosensors is not strong, which results in the peptoid small molecules cannot be used as the probe molecules. Antibodies have characteristics of tight binding to biosensors, however, the arrangement of the antibody molecules is disordered, and the arrangement direction of the antibody molecules on the surface of the sensor is random and is difficult to be controlled, as a result, the specificity of the antibody molecule is lower. In addition, the cost of the antibody is higher. The inventors of the present disclosure found that an oligomer formed by peptoid small molecules and antibody-like can well bind with the peptoid small molecule and the antibody, that is, the oligomer not only has the characteristics of tight binding of the antibody to the biosensor, but also can form peptoid small molecules on the surface of the sensor in an orderly manner. In addition, the molecular probe formed by the oligomer has strong affinity with the tumor cells, and the oligomer cannot be enzymatically hydrolyzed, which ensures the activity of natural living samples.

By comparison of peptoid with peptide, the peptide is composed of α-amino acids which acting as structural units, while the peptoid is composed of N-substituted glycines which acting as structural units. A peptoid compound has good biological activity and pharmaceutical property, and the peptoid compound can effectively detect or inhibit deterioration in living experiments and have good cell membrane permeability. At present, a more mature peptide synthesis technology is "subunit synthesis" technology.

At least one embodiment of the present disclosure provides a peptoid compound, and the peptoid compound comprises: a cysteine (Cys) subunit, a butanediamine (Nlys) subunit, a 3,4-methylenedioxybenzylamine (Npip) subunit, a 3-aminopropanic acid (Nce) subunit, and a 1-naphthylamine (Na) subunit.

For example, molecular structures of each of the subunits are as follows:

(cysteine, Cys)  (butanediamine, Nlys)  (3-aminopropanic acid, Nce)

(3,4-methylenedioxybenzylamine, Npip)  (1-napthylamine, Na)

For example, in the peptoid compound provided by at least one embodiment of the present disclosure, the peptoid compound comprises subunits in an order of: cysteine (Cys) subunit-butanediamine (Nlys) subunit-butanediamine (Nlys) subunit-butanediamine (Nlys) subunit-3,4-methylenedioxybenzylamine (Npip) subunit-3-aminopropanic acid (Nce) subunit-1-naphthylamine (Na) subunit.

For example, the peptoid compound has a structure of Formula (I):

At least one embodiment of the present disclosure further provides a manufacturing method of a peptoid compound, and the manufacturing method comprises synthesizing the subunits by a solid phase synthetic method.

Figure 1:
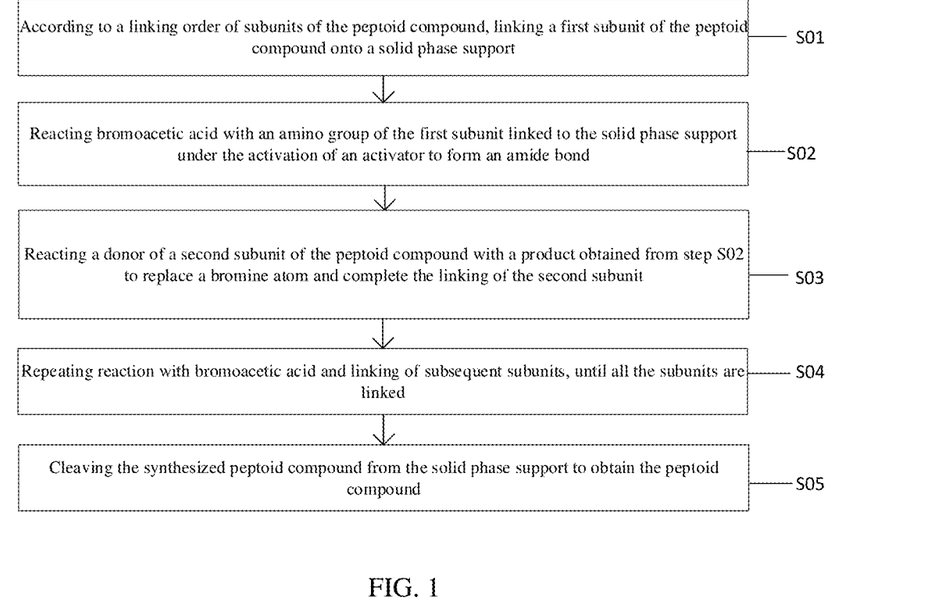
FIG. 1 is a flowchart of a manufacturing method of a peptoid compound provided by an embodiment of the present disclosure.

For example, FIG. 1 is a flowchart of a manufacturing method of a peptoid compound provided by an embodiment of the present disclosure. As illustrated in FIG. 1, the manufacturing method comprises:

step S01: according to a linking order of subunits of the peptoid compound, linking a first subunit of the peptoid compound onto a solid phase support;

step S02: reacting bromoacetic acid with an amino group of the first subunit linked to the solid phase support under the activation of an activator to form an amide bond;

step S03: reacting a donor of a second subunit of the peptoid compound with a product obtained from step S02 to replace a bromine atom and complete the linking of the second subunit;

step S04: repeating reaction with bromoacetic acid and linking of subsequent subunits, until all the subunits are linked, and the subunits are linked in an order of: cysteine (Cys), tert-butoxycarbonyl (Boc)-protected butanediamine (Nlys), Boc-protected butanediamine (Nlys), Boc-protected butanediamine (Nlys), 3,4-methylenedioxybenzylamine (Npip), 3-aminopropanic acid (Nce), and 1-naphthylamine (Na).

step S05: cleaving the synthesized peptoid compound from the solid phase support to obtain the peptoid compound.

For example, the solid phase support is Rink amide AM resin.

For example, the solid phase support is subject to a swelling treatment before linking the first subunit of the peptoid to the solid phase support.

For example, in a case that the solid phase support is the Rink amide AM resin, it is swollen firstly, and then deprotected with hexahydropyridine so as to expose the amino group of the Rink amide AM resin.

For example, the process of linking the first subunit of the peptoid to the solid phase support is performed under the action of a condensing agent and an activator.

Formula (I)

For example, the peptide compound can be used as a probe molecule to specifically recognize the HER2 protein, that is, the peptide compound can bind to the HER2 protein which is the marker of the breast cancer for detecting the breast cancer.

For example, the condensing agent is at least one of 2-(3'-N-oxo-benzotriazole)-1,1',3,3'-tetramethylurea hexafluorophosphate hexafluorophosphate, O-benzotriazole-N,N,N',N'-tetramethylurea tetrafluoroborate and 1-hydroxylbenzotriazole.

For example, the activator used in step S01 is N-methylmorpholine.

For example, the activator used in step S02 is N,N'-diisopropylcarbodiimide (DIC) or dicyclohexylcarbodiimide.

For example, the reaction temperature in step S02 is 20° C. to 40° C., for example, 20° C., 21° C., 23° C., 24° C., 25° C., 33° C., 34° C., 36° C., 38° C. or 40° C.

For example, the reaction time in step S02 is 10 min to 100 min, for example, 10 min, 15 min, 20 min, 25 min, 30 min, 35 min, 40 min, 50 min, 60 min, 70 min, 80 min, 90 min or 100 min.

For example, the donor in step S03 refers to a compound of the peptoid subunit. For example, the donor of the cysteine subunit is cysteine, the donor of the butanediamine subunit is butanediamine, the donor of the 3,4-methylenedioxybenzylamine subunit is 3,4-methylenedioxybenzylamine subunit, the donor of the 3-aminopropanic acid subunit is 3-aminopropanic acid, and the donor of the 1-naphthylamine subunit is 1-naphthylamine.

For example, the reaction temperature in step S03 is 20° C. to 40° C., for example, 20° C., 21° C., 23° C., 24° C., 25° C., 33° C., 34° C., 36° C., 38° C. or 40° C.

For example, the reaction time in step S03 is 30 min to 180 min, for example, 30 min, 35 min, 45 min, 50 min, 55 min, 60 min, 65 min, 70 min, 80 min, 90 min, 100 min, 120 min, 140 min, 150 min, 160 min, 170 min or 180 min.

For example, the repeating the linking of the bromoacetic acid and the subsequent submits in step S04 refers to repeating the step S04 and the step S03, except that the linked subunits are the subsequent subunits.

For example, the cleaving agent used in the cleaving of step S05 comprises components by weight percent of: 95 wt % of trifluoroacetic acid, 2.5% of ultrapure water, and 2.5% of triisopropylsilane.

For example, in the process of manufacturing the peptoid compound, groups that are not involved in the linking reaction can be protected to ensure the accuracy of the linking sites, thereby allowing the reaction to run more accurately and smoothly. Then, after all the subunits are linked, de-protection is performed to remove the protective groups.

For example, the synthesizing of the peptoid compound by the solid phase synthetic method particularly comprises:

(1) swelling the Rink amide AM resin (with a substitution level of 0.3 mmol/g), followed by deprotection with hexahydropyridine, mixing cysteine with an equivalent mole of 2-(3'-N-oxo-benzotriazole)-1,1',3,3'-tetramethyluronium hexafluorophosphate for coupling under the activation of N-methylmorpholine;

(2) adding 10 mL of bromoacetic acid with a concentration of 2 mol/L and 10 mL of N,N'-diisopropylcarbodiimide (DIC) with a concentration of 3.2 mol/L into the Rink amide AM resin (a starting resin for peptide synthesis, with a substitution level of 0.3 mmol/g), and allowing the mixture to react at 37° C. for 30 min so as to acylate the amine group at the terminal of the resin;

(3) additionally adding 10 mL of a primary amine with a concentration of 2 mol/L into the mixture, and then allowing the mixture to react at 37° C. for 90 min so as to replace the bromine atom by nucleophilic substitution reaction to complete the synthesis of a subunit;

(4) repeating step (2) and step (3) until the synthesis of the remaining units is completed;

(5) after the synthesis is completed, removing the side chain protective group, and cleaving the peptoid compound from the resin by a mixture of trifluoroacetic acid with a mass percentage of 95%, ultrapure water with a mass percentage of 2.5%, and triisopropylsilane with a mass percentage of 2.5%, and the peptoid compound is for use in future.

For example, the manufacturing method of the peptoid compound provided by at least one embodiment of the present disclosure, further comprises a step of purifying the obtained product as needed. The purification method is not particularly limited, and purification can be performed by methods for purifying similar products, such as precipitation, filtration, dialysis, gel permeation chromatography and so on.

At least one embodiment of the present disclosure further provides an oligomer, and the oligomer comprises a molecular structure formula of:

in which 10≥n1≥3, 10≥n2≥3, n1=n2, and both n1 and n2 are natural numbers.

For example, the oligomer comprises: β-phenylethylamine subunit, biphenylethylamine subunit, cysteine (Cys) subunit, butanediamine (Nlys) subunit, 3,4-methylenedioxybenzylamine (Npip) subunit, 3-aminopropanic acid (Nce) subunit, 1-naphthylamine (Na) subunit, and ethylenediamine subunit.

For example, the subunits have the following structural formulas respectively:

(β-phenylethyl amine)  (biphenylethylamine)

(cysteine, Cys)  (butanediamine, Nlys)

(3-aminopropanic acid, Nce)  (ethylenediamine)

(3,4-methylenedioxybenzamine, Npip)

(1-naphthylamine, Na)

For example, in the oligomer provided by at least one embodiment of the present disclosure, the oligomer comprises subunits arranged in an order of: [β-phenylethyl amine subunit-3-aminopropanic acid subunit-biphenylethylamine subunit-3-aminopropanic acid subunit]$n_2$-β-phenylethyl amine subunit-cysteine (Cys) subunit-butanediamine (Nlys) subunit-butanediamine (Nlys) subunit-butanediamine (Nlys) subunit-3,4-methylenedioxybenzylamine (Npip) subunit-3-aminopropanic acid (Nce) subunit-1-naphthylamine (Na) subunit-biphenylethylamine subunit-ethylenediamine subunit-[β-phenylethylamine subunit-ethylamine subunit-biphenylethylamine subunit-ethylamine subunit]$n_1$.

At least one embodiment of the present disclosure further provides a manufacturing method of an oligomer, and the oligomer is synthesized by a solid phase subunit synthetic method.

Figure 2:
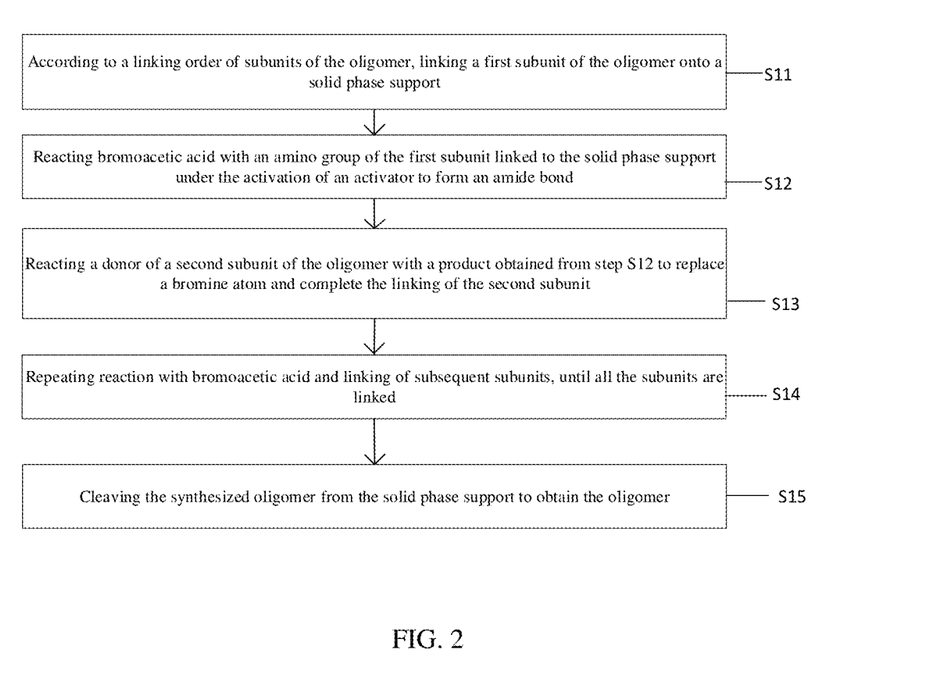
FIG. 2 is a flowchart of a manufacturing method of an oligomer provided by an embodiment of the present disclosure.

For example, FIG. 2 is a flowchart of a manufacturing method of an oligomer provided by an embodiment of the present disclosure. As illustrated in FIG. 2, the manufacturing method of the oligomer comprises:

step S11: according to a linking order of subunits of the oligomer, linking a first subunit of the oligomer onto a solid phase support;

step S12: reacting bromoacetic acid with an amino group of the first subunit linked to the solid phase support under the activation of an activator to form an amide bond;

step S13: reacting a donor of a second subunit of the oligomer with a product obtained from step S12 to replace a bromine atom and complete the linking of the second subunit;

step S14: repeating reaction with bromoacetic acid and linking of subsequent subunits, until all the subunits are linked;

step S15: cleaving the synthesized oligomer from the solid phase support to obtain the oligomer.

For example, the oligomer comprises any one of the peptoid compounds mentioned in the above embodiments, and further comprises auxiliary chains formed at the left side and auxiliary chains formed the right side of the peptoid compound respectively. All the auxiliary chains formed at the left side of the peptoid compound comprise amino groups, and all the auxiliary chains formed at the right side of the peptoid compound comprise carboxyl groups. Both the auxiliary chains formed at the left side and the auxiliary chains formed at the right side of the peptoid compound contribute to form the oligomer in a two-dimensional layered structure, so that the peptoid compound in the middle exposes on the surface of the sensor and is used as a probe molecule for detecting the HER2 protein. Furthermore, both the auxiliary chains formed at the left side and the auxiliary chains formed at the right side of the peptoid compound allow the oligomer to arrange more regularly.

For example, the condensing agent(s) and the activator(s) used in various steps of the process of preparing the oligomer can refer to the relevant description of the process of preparing the peptoid compound, which are omitted herein.

For example, in the oligomer, n1=n2=3, n1=n2=4, n1=n2=6, n1=n2=8, or n1=n2=10.

It should be noted that, in the case that both n1 and n2 are less than 3, a problem that the chain length is too short to assemble is occurred. In the case that both n1 and n2 are greater than 10, the formed chain is too long, and the density of the peptoid compound inserted into the middle of the oligomer is too low, and thus a problem of reduced affinity is occurred, so that the problem of specific binding of the oligomer to HER2 protein on the CTCs cannot be achieved.

First Example

A manufacturing method of an oligomer with a structure of formula:

particularly comprises:

(1) swelling the Rink amide AM resin (a starting resin for peptide synthesis, with a substitution level of 0.3 mmol/g), followed by deprotection with hexahydropyridine, mixing β-phenylethyl amine with an equivalent mole of 1-hydroxyl benzotriazole for coupling under the activation of N-methylmorpholine;

(2) adding 10 mL of bromoacetic acid with a concentration of 2 mol/L and 10 mL of N,N'-diisopropylcarbodiimide (DIC) with a concentration of 3.2 mol/L into the Rink amide AM resin, and allowing the mixture to react at 38° C. for 30 min so as to acylate the amine group at the terminal of the resin;

(3) additionally adding 10 mL of a primary amine with a concentration of 2 mol/L into the mixture, and then allowing the mixture to react at 37° C. for 90 min so as to replace the bromine atom by nucleophilic substitution reaction to complete the synthesis of a subunit;

(4) repeating step (2) and step (3) until the synthesis of the remaining units is completed;

(5) after the synthesis is completed, removing the side chain protective group, and cleaving the peptoid compound from the resin by a mixture of trifluoroacetic acid with a mass percentage of 95%, ultrapure water with a mass percentage of 2.5%, and triisopropylsilane with a mass percentage of 2.5%, and the oligomer is for use in future.

In the process of forming the oligomer having the above mentioned structure, the subunits are linked in an order of: β-phenylethyl amine, 3-aminopropanic acid, biphenylethylamine, 3-aminopropanic acid; β-phenylethyl amine, 3-aminopropanic acid, biphenylethylamine, 3-aminopropanic acid; β-phenylethyl amine, 3-aminopropanic acid, biphenylethylamine, 3-aminopropanic acid; β-phenylethyl amine, cysteine (Cys), tert-butoxycarbonyl (Boc)-protected butanediamine (Nlys), Boc-protected butanediamine (Nlys), Boc-protected butanediamine (Nlys), 3,4-methylenedioxy benzamine (Npip), 3-aminopropanic acid (Nce), 1-naphthylamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine.

It should be noted that, tert-butoxycarbonyl (t-Boc or Boc) is a protecting group for protecting amino groups.

For example, the oligomer can be dissolved into a mixed solution comprising dimethylsulfoxide (DMSO) and water ($H_2O$), and dimethylsulfoxide and water are in a molar ratio of 2:1 to a final concentration of 2 mM.

Second Example

A manufacturing method of an oligomer with a structure of formula:

-continued particularly comprises:

(1) swelling the Rink amide AM resin (a starting resin for peptide synthesis, with a substitution level of 0.3 mmol/g), followed by deprotection with hexahydropyridine, mixing β-phenylethyl amine with an equivalent mole of 1-hydroxyl benzotriazole for coupling under the activation of N-methylmorpholine;

(2) adding 20 mL of bromoacetic acid with a concentration of 2 mol/L and 15 mL of N,N'-diisopropylcarbodiimide (DIC) with a concentration of 3.2 mol/L into the Rink amide AM resin, and allowing the mixture to react at 38° C. for 30 min so as to acylate the amine group at the terminal of the resin;

(3) additionally adding 10 mL of a primary amine with a concentration of 2 mol/L into the mixture, and then allowing the mixture to react at 37° C. for 90 min so as to replace the bromine atom by nucleophilic substitution reaction to complete the synthesis of a subunit;

(4) repeating step (2) and step (3) until the synthesis of the remaining units is completed;

(5) after the synthesis is completed, removing the side chain protective group, and cleaving the peptoid compound from the resin by a mixture of trifluoroacetic acid with a mass percentage of 95%, ultrapure water with a mass percentage of 2.5%, and triisopropylsilane with a mass percentage of 2.5%, and the oligomer is for use in future.

In the process of forming the oligomer having the above mentioned structure, the subunits are linked in an order of: β-phenylethyl amine, 3-aminopropanic acid, biphenylethylamine, 3-aminopropanic acid; β-phenylethyl amine, 3-aminopropanic acid, biphenylethylamine, 3-aminopropanic acid; β-phenylethyl amine, 3-aminopropanic acid, biphenylethylamine, 3-aminopropanic acid; β-phenylethyl amine, 3-aminopropanic acid, biphenylethylamine, 3-aminopropanic acid; β-phenylethyl amine, 3-aminopropanic acid, biphenylethylamine, 3-aminopropanic acid; β-phenylethyl amine, 3-aminopropanic acid, biphenylethylamine, 3-aminopropanic acid; β-phenylethyl amine, cysteine (Cys), Boc-protected butanediamine (Nlys), Boc-protected butanediamine (Nlys), Boc-protected butanediamine (Nlys), 3,4-methylenedioxy benzamine (Npip), 3-aminopropanic acid (Nce), 1-naphthylamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine.

For example, the oligomer can be dissolved into a mixed solution comprising dimethylsulfoxide (DMSO) and water ($H_2O$), and dimethylsulfoxide and water are in a molar ratio of 2:1 to a final concentration of 2 mM.

Third Example

A manufacturing method of an oligomer with a structure of Formula:

particularly comprises:

(1) swelling the Rink amide AM resin (a starting resin for peptide synthesis, with a substitution level of 0.3 mmol/g), followed by deprotection with hexahydropyridine, mixing β-phenylethyl amine with an equivalent mole of 1-hydroxyl benzotriazole for coupling under the activation of N-methylmorpholine;

(2) adding 25 mL of bromoacetic acid with a concentration of 2 mol/L and 22 mL of N,N'-diisopropylcarbodiimide (DIC) with a concentration of 3.2 mol/L into the Rink amide AM resin, and allowing the mixture to react at 38° C. for 30 min so as to acylate the amine group at the terminal of the resin;

(3) additionally adding 10 mL of a primary amine with a concentration of 3 mol/L into the mixture, and then allowing the mixture to react at 37° C. for 90 min so as to replace the bromine atom by nucleophilic substitution reaction to complete the synthesis of a subunit;

(4) repeating step (2) and step (3) until the synthesis of the remaining units is completed;

(5) after the synthesis is completed, removing the side chain protective group, and cleaving the peptoid compound from the resin by a mixture of trifluoroacetic acid with a mass percentage of 95%, ultrapure water with a mass percentage of 2.5%, and triisopropylsilane with a mass percentage of 2.5%, and the oligomer is for use in future.

In the process of forming the oligomer having the above mentioned structure, the subunits are linked in an order of:

β-phenylethyl amine, 3-aminopropanic acid, biphenylethylamine, 3-aminopropanic acid β-phenylethyl amine, 3-aminopropanic acid, biphenylethylamine, 3-aminopropanic acid β-phenylethyl amine, 3-aminopropanic acid, biphenylethylamine, 3-aminopropanic acid β-phenylethyl amine, 3-aminopropanic acid β-phenylethyl amine, 3-aminopropanic acid, biphenylethylamine, 3-aminopropanic acid β-phenylethyl amine, 3-aminopropanic acid, biphenylethylamine, 3-aminopropanic acid β-phenylethyl amine, 3-aminopropanic acid β-phenylethyl amine, 3-aminopropanic acid, biphenylethylamine, 3-aminopropanic acid; β-phenylethyl amine, 3-aminopropanic acid, biphenylethylamine, 3-aminopropanic acid; β-phenylethyl amine, cysteine (Cys), Boc-protected butanediamine (Nlys), Boc-protected butanediamine (Nlys), Boc-protected butanediamine (Nlys), 3,4-methylenedioxy benzamine (Npip), 3-aminopropanic acid (Nce), 1-naphthylamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine; β-phenylethyl amine, Boc-protected ethylenediamine, biphenylethylamine, Boc-protected ethylenediamine.

For example, the oligomer can be dissolved into a mixed solution comprising dimethylsulfoxide (DMSO) and water ($H_2O$), and dimethylsulfoxide and water are in a molar ratio of 2:1 to a final concentration of 2 mM.

The process of synthesizing the oligomer provided by the embodiments of the present disclosure is simple. The oligomer has relatively strong binding capacity with the HER2, it is able to effectively screen the serum of the patient with the breast cancer and the serum of normal human by the HER2 protein in the serum. It is able to specifically recognize the HER2 protein on the surface of CTCs of the patient with the breast cancer, which provides a favorable guarantee for capturing the corresponding CTCs with high sensitivity. For example, it is feasible to design a molecular probe having high affinity and sensitivity to the HER2 proteins.

For example, a method of detecting the binding capacity of the oligomer with the HER2 protein by means of surface plasmon resonance imaging technology comprises the follows.

(1) The oligomers were dissolved into ddH2O to a concentration of 1 μM to 1000 μM respectively;

(2) The oligomer solutions were dropped on surfaces of 3D chips, and each of the samples was repeatedly dropped 3 times, the chips were placed at 4° C. for 12 hours, and successively washed with 10×PBS buffer solution, 1×PBS buffer solution, and ultrapure water, and then blocked with 1M aminoethanol hydrochloride for 30 min, rinsed with 5× ultrapure water, and finally dried under nitrogen.

(3) The chips were installed on a SPRi instrument, the SPRi angle was measured and the SPRi angle was adjusted to an optimal optical position, relevant detection points were selected in detection regions, and sample points and blank points were included in the relevant detection points, and the experimental flow rate was set as 2 μL/s;

(4) PBS was selected as a buffer solution flowing into a flow cell until the baseline was stable, then detections were performed on the HER2 protein with concentrations of 2.2 μM, $4.6 \times 10^{-1}$ μM, $9.1 \times 10^{-2}$ μM, $1.8 \times 10^{-2}$ μM, and $3.6 \times 10^{-3}$ μM successively. The binding time was 300 seconds respectively; and the dissociation time was 300 seconds respectively. After the detection of the previous concentration of HER2 protein was completed, phosphoric acid was passed in to make the test solution return to the initial state, and then the detection of the next concentration of HER2 protein was performed.

Figure 3:
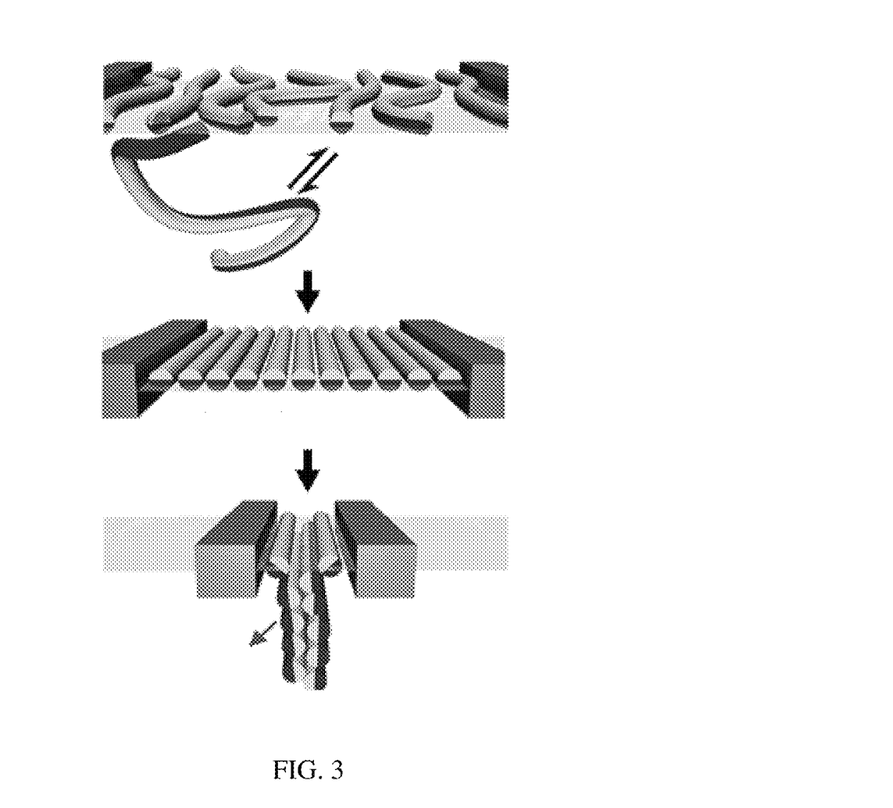
FIG. 3 is a schematic view of a formation process of a two-dimensional oligomer provided by an embodiment of the present disclosure.

For example, FIG. 3 is a schematic view of a formation process of a two-dimensional oligomer provided by an embodiment of the present disclosure. As illustrated in FIG. 3, the process of forming the two-dimensional oligomer comprises: placing the oligomer provided by any one of the embodiments of the present disclosure in a Langmuir tank, in which the oligomer comprises a hydrophilic end and a hydrophobic end. In the absence of external force, the oligomers are randomly arranged at the interface between the gas and the liquid. Then, an external force is applied to the randomly arranged oligomers to allow them to be orderly arranged at the interface between the gas and the liquid so that the oligomers are pressed under the interface between the gas and the liquid. Under the interface between the gas and the liquid, the hydrophilic ends of the oligomers expose on the outside, and the hydrophobic ends form on the inside, thereby the two-dimensional oligomers are formed.

Figure 4A:
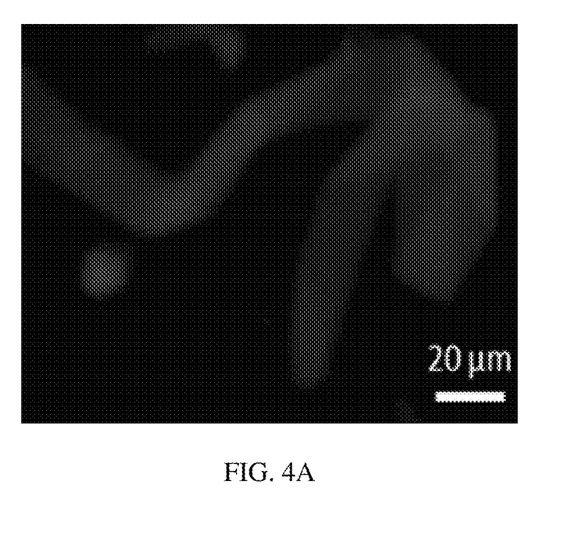
FIG. 4A is an atomic force microscopic image of an oligomer provided by an embodiment of the disclosure.
Figure 4B:
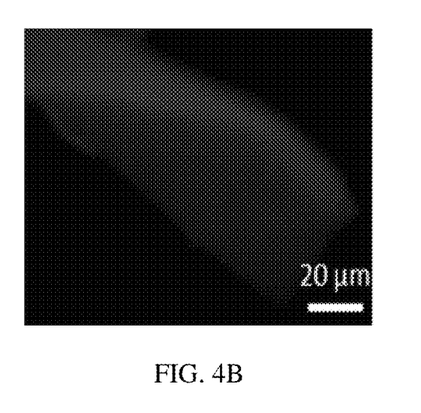
FIG. 4B is an atomic force microscopic image of another oligomer provided by an embodiment of the present disclosure.

A process of forming an oligomer nanosheet is as follows: the oligomer with a concentration of 2 mM prepared according to any one of the first example to the third example is dissolved in 10 mM 4-hydroxyethylpiperazine ethane sulfonic acid and 100 mM sodium chloride, and a buffer solution is added to adjust that pH of the solution is 8.0 and makes that the final concentration of the oligomer is 1 μM to 100 μM, for example, 20 μM. Then, a manual shaking method is used, the peptoid solution is stably stored at room temperature for 22 hours, then manually shake the peptoid solution for 30 seconds, and then stabilize the peptoid solution for 1 minute, the shaking process and the stabilization process are repeated for 5 times respectively; or a machine shaking method is used, a tube containing the oligomer solution is slowly rotated from a horizontal direction to a perpendicular direction (at 0.6 rpm), and the tube is rotated every 450 seconds; nile red is added to the oligomer nanosheet solution to a final concentration of 1 μM, the oligomer solution is placed on 1% agar by a mass percentage, and the oligomer solution is observed under a fluorescent microscope (Vert.A1, Carl Zeiss Far East, Germany) The results are shown in FIG. 4A and FIG. 4B, and obvious nanosheet structures are observed.

Figure 5:
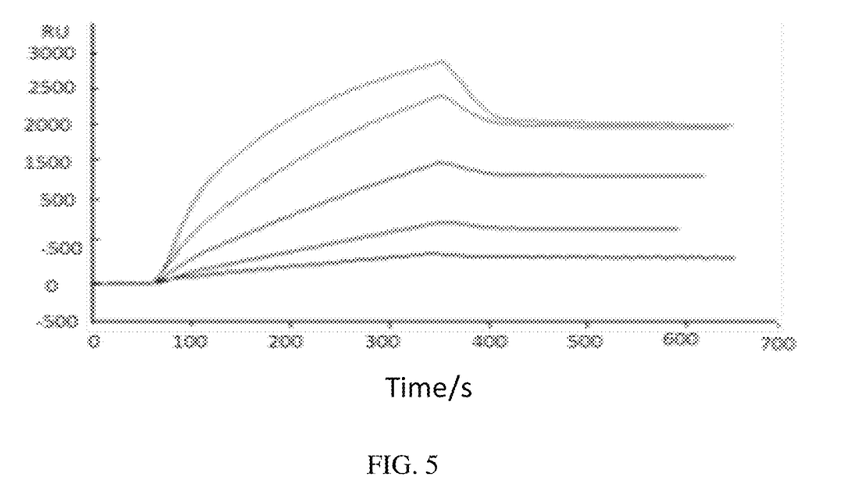
FIG. 5 is a graph showing results of surface plasmon resonance detection of an oligomer provided by an embodiment of the present disclosure bonded to HER2 protein with concentrations of 2.2 µM, $4.6 \times 10^{-1}$ µm, $9.1 \times 10^{-2}$ µM, $1.8 \times 10^{-2}$ µM, and $3.6 \times 10^{-3}$ µM respectively.

For example, FIG. 5 is a graph showing results of surface plasmon resonance detection of an oligomer provided by an embodiment of the present disclosure bonded to HER2 protein with concentrations of 2.2 μM, $4.6 \times 10^{-1}$ μM, $9.1 \times 10^{-2}$ μM, $1.8 \times 10^{-2}$ μM, and $3.6 \times 10^{-3}$ μM respectively, in which, ARU represents the binding signal after the mobile phase passing through the array minus the baseline signal of the initial PBS buffer solution, the curve is the detection result of PlexArray HT, the fitting line is obtained by BlAevalution 4.1. ARU is a dimensionless unit, and reflects the binding signal intensity in the surface plasmon resonance imaging By fitting, the equilibrium dissociation constant KD is $3.76 \times 10^{-10}$ mol/L, which indicates that the oligomer has a fairly high affinity level with the HER2 protein.

The specific steps of using plasmon resonance imaging technology to test the detection of the oligomers on the serum of the patient with breast cancer, the serum of the patient with gastric cancer or the serum of the patient with ovarian cancer and the serum of normal human are as follows.

(1) The oligomer solutions were dropped on surfaces of 3D chips, and each of the samples was repeatedly dropped 3 times respectively, the chips were placed at 4° C. for 12 hours, and successively washed with 10×PBS buffer solution (phosphate buffered saline), 1×PBS buffer solution, and ultrapure water, and then blocked with 1M aminoethanol hydrochloride for 30 min, rinsed with 5× ultrapure water, and finally dried under nitrogen. The above chips were installed on a SPRi instrument, the SPRi angle was measured and the SPRi angle was adjusted to an optimal optical position, relevant detection points were selected in detection regions, and sample points and blank points were included in the relevant detection points, and the experimental flow rate was set as 2 μL/s.

(2) PBS was selected as the buffer solution flowing into a flow cell until the baseline was stable, and then the serum of different patients and the serum of normal people were passed into and diluted (1:5000) separately. The binding time was 300 seconds respectively; and the dissociation time was 300 seconds respectively. After each of the samples was tested, phosphate and proteinase K were passed in to make the test solution return to the initial state, and then the detection of the next kind of serum was performed.

The patient with breast cancer, the patient with gastric cancer, or the patient with ovarian cancer is distinguished from normal people based on the binding strength of the oligomer to the signal of surface plasmon resonance imaging.

For example, a process of testing the sensitivity of the breast cancer diagnosing system for detecting serum by means of surface plasmon resonance imaging technology particularly comprises the steps as follows.

(1) The oligomer solutions were dropped on surfaces of 3D chips, and each of the samples was repeatedly dropped 3 times respectively, the chips were placed at 4° C. for 12 hours, and successively washed with 10×PBS buffer solution, 1×PBS buffer solution, and ultrapure water, and then blocked with 1M aminoethanol hydrochloride for 30 min, rinsed with 5× ultrapure water, and finally dried under nitrogen. The above chips were installed on a SPRi instrument, the SPRi angle was measured and the SPRi angle was adjusted to an optimal optical position, relevant detection points were selected in detection regions, and sample points and blank points were included in the relevant detection points, and the experimental flow rate was set as 2 μL/s.

(2) PBS was selected as the buffer solution flowing into a flow cell until the baseline was stable, and then the serum dilution of different patients and the serum dilution of normal people were passed into separately. The concentrations of the serum dilution of different patients and normal people were 1:2000, 1:4000, 1:8000, 1:16000 and 1:32000 respectively. The binding time was 300 seconds respectively; and the dissociation time was 300 seconds respectively. After each of the samples was tested, phosphate and proteinase K were passed in to make the test solution return to the initial state, and then the detection of the next kind of serum was performed.

The detection results indicate that when the serum dilution ratio is less than or equal to 1:8000, the HER2-overexpressed patients with breast cancer, the HER2-overexpressed patient with ovarian cancer, the HER2-overexpressed patient with stomach cancer are apparently distinguished from normal person, which shows that it has an extremely high sensitivity for detecting serum.

For example, the 3D chips are the PlexArray HT 3D chips commercially available from Plexera Bioscience Inc., U.S.A.

For example, the oligomers are self-assembled at the interfaces between the gas and the liquid to form peptoid nanosheets with specific identification of the HER2 proteins on its surface. The peptoid nanosheets serve as scaffolds and support peptoid compounds as molecular probes to recognize the HER2 proteins. Such peptoid nanosheets in combination with the surface plasmon resonance technology can be used for detecting breast cancer.

For example, the oligomer is two-dimensional nanosheet material, so that the oligomer can be coupled onto a sensor, and the peptoid compound with affinity is on the surface of the sensor.

The two-dimensional peptoid nanomaterials play an increasingly important role in biology and electronics, such as, sensing, template growth and filtration, and as a protein mimetic to test the molecular recognition and catalytic capabilities of proteins. The Langmuir tank experimental device reveals that the formation of the peptoid nanosheets is a thermodynamic equilibrium process of self-assembly of peptoid molecules and conversion of external mechanical energy into chemical energy of the peptoid molecules.

For example, the pharmaceutical composition further comprises: any one of the oligomers mentioned above, and a pharmaceutically acceptable adjuvant.

For example, the adjuvant comprises at least one of an excipient, a diluent, a carrier, a flavoring agent, a binder, and a filler.

For example, the excipient is emulsion or oily suspension, or polyalkylene glycol such as polypropylene glycol.

At least one embodiment of the present disclosure further provides use of any one of the pharmaceutical compositions mentioned above in the preparation of a medicament for detecting or diagnosing a disease related to tyrosine kinase HER2.

For example, the disease comprises at least one of breast cancer, gastric cancer, and ovarian cancer.

At least one embodiment of the present disclosure further provides a kit for identifying circulating tumor cells, and the kit comprises: a housing, a microfluidic chip disposed in the housing, and a fluorescent probe disposed in the housing, and the fluorescent probe is any one of the oligomers mentioned above with a fluorescent label.

For example, the microfluidic chip comprises a micro-valve control layer, and a micro-value film layer. The micro-valve control layer is provided with six holes passing through the control layer and three gas channels, and three holes are sample adding holes, which communicate with a substrate for the inflow and outflow of samples and reagents; and the remaining three holes communicate with the three gas channels, respectively, and used for injecting the gas and controlling the opening and closing of the micro-valve. The micro-valve film layer is provided with three holes passing through the film layer, which correspondingly communicate with the three sample adding holes in the above mentioned micro-valve control layer respectively.

For example, both an outer contour dimension of the micro-valve control layer and an outer contour dimension of the micro-valve film layer should match the dimension of the substrate.

For example, fluorescent probes are used for identifying cells, and the molecular probes having fluorescent probes in the embodiments of the present disclosure are oligomers labeled with fluorescent molecules.

For example, the type of the fluorescent group is not particularly limited in the embodiments of the present disclosure, as long as the oligomer modified by the fluorescent group has fluorescent properties and can also realize the basic functions of the oligomer. The oligomers in the embodiments of the present disclosure may be modified with one fluorescent group or more fluorescent groups. For example, a single fluorescently labeled oligomer is obtained by modifying with one fluorescent group, or a double fluorescently labeled oligomer is obtained by modifying with two fluorescent groups. In some embodiments, the fluorescent groups may be selected, without limitation, from the group consisting of blue fluorescent probe dye, near infrared fluorescent dye, green fluorescent dye and so on. For example, a coumarin-containing fluorescent group, an anthracene-containing fluorescent group, a rhodamine fluorescent group, a phenanthroimidazole fluorescent group, a naphthalene-containing fluorescent group, an isothiocyanate fluorescein, a carboxyl fluorescein (FAM), a thiocyanate fluorescein (FITC), dansyl chloride, 2,4-dinitrobenzene (Dnp), carbo-xyrhodamine 110, Texas Red, pentamethine cyanine dye (Cy5), and heptamethine cyanine dye (Cy7) and so on.

For example, in addition to the microfluidic chip and the fluorescent probe (probe), the kit may further comprise a fluorescent microscope (a fluorescent imaging system), a self-developed image analysis software (an analysis and counting system), and a pump to constitute a complete system so as to complete the treatment of blood samples, as well as the separation and counting of the circulating tumor cells.

For example, the fluorescent microscope is used for detecting whether the cells in the micro V-shaped positioning array comprise fluorescence, and full coverage fluorescence imaging is performed on the functional region to obtain multi-channel fluorescence images.

For example, the self-developed image analysis software is used for analyzing the images acquired by the fluorescence microscope and obtaining the corresponding number of the CTCs. The software accurately calculates the parameters including size, area, aspect ratio, and roundness of the cells and so on in the image, selects the CTCs that meet the requirements, and meanwhile counts the CTCs. According to a self-programmed algorithm to screen and identify the localized cells, and to identify the circulating tumor cells which meet the labeled fluorescent characteristics, and count the cells, then the positions of the cells and the enlarged cell images are reported.

Embodiments of the present disclosure provide a peptoid compound, a manufacturing method of a peptoid compound, an oligomer, a pharmaceutical composition, use of the pharmaceutical composition in the preparation of a medicament for detecting or diagnosing a disease related to tyrosine kinase HER2, and a kit for identifying circulating tumor cells, which have at least one of the following beneficial effects:

(1) in the oligomer provided by at least one embodiment of the present disclosure, the oligomers have strong binding ability to the HER2 proteins on the surfaces of the CTCs. An equilibrium dissociation constant KD, which is obtained by the surface plasmon resonance technique, in the binding kinetic constant of the oligomers to the HER2 proteins is on the order of $10^{-10}$ mol/L.

(2) in the oligomer provided by at least one embodiment of the present disclosure, the surface plasmon resonance technique is used to detect the blood signal intensity of the oligomers on the patient with breast cancer and the blood signal intensity of normal person. It can be found that using the oligomers can clearly distinguish the patient with breast cancer from normal person.

(3) in the oligomer provided by at least one embodiment of the present disclosure, the diagnostic technology based on the oligomer to diagnose the patient with breast cancer can realize non-invasive and label-free rapid diagnosis.

(4) the synthesis method of the peptoid compound and the oligomer provided by at least one embodiment of the present disclosure is simple, the preparation efficiency is high, and the production cost is low.

The following points required to be explained:
(1) the drawings of the embodiments of the present disclosure only relate to the structures related to the embodiments of the present disclosure, and other structures can refer to the general design.
(2) for the sake of clarity, in the drawings used to describe the embodiments of the present disclosure, the thickness of layers or areas is enlarged or reduced, that is, the drawings are not drawn according to the actual scale.

(3) without conflict, the embodiments of the present disclosure and the features in the embodiments may be combined with each other to obtain new embodiments.

What are described above is related to only the illustrative embodiments of the present disclosure and not limitative to the protection scope of the present application. Therefore, the protection scope of the present application shall be defined by the accompanying claims.

What is claimed is:

1. A peptoid compound, wherein the peptoid compound has a structure of Formula (I):

Formula I (1) according to a linking order of subunits of the peptoid compound, linking a first subunit of the peptoid compound onto a solid phase support;

(2) reacting bromoacetic acid with an amino group of the first subunit linked to the solid phase support under the activation of an activator to form an amide bond;

(3) reacting a donor of a second subunit of the peptoid compound with a product obtained from step (2) to replace a bromine atom and complete the linking of the second subunit;

(4) repeating reaction with bromoacetic acid and linking of subsequent subunits, until all the subunits are linked;

(5) cleaving the synthesized peptoid compound from the solid phase support to obtain the peptoid compound.

2. An oligomer, comprising a molecular structure formula of:

wherein 10≥n1≥3, 10≥n2≥3, n1=n2, and both n1 and n2 are natural numbers.

3. The oligomer according to claim 2, wherein the molecular structure formula of the oligomer is:

-continued

4. A pharmaceutical composition, comprising:
   the oligomer according to claim 3; and
   a pharmaceutically acceptable adjuvant.

5. The pharmaceutical composition according to claim 4, wherein the adjuvant comprises at least one of an excipient, a diluent, a carrier, a flavoring agent, a binder, and a filler.

6. A kit for identifying circulating tumor cells, comprising: a housing, a microfluidic chip disposed in the housing, and a fluorescent probe disposed in the housing, wherein the fluorescent probe is the oligomer according to claim 2 with a fluorescent label.

* * * * *